United States Patent
Kerboul et al.

(10) Patent No.: US 9,931,127 B2
(45) Date of Patent: Apr. 3, 2018

(54) ADJUSTABLE RONGEUR

(71) Applicant: Specialty Surgical Instrumentation, Inc., Antioch, TN (US)

(72) Inventors: Guillaume Kerboul, Gloucestershire (GB); Jim Truscott, Gloucestershire (GB); Stuart Weekes, Gloucestershire (GB)

(73) Assignee: Specialty Surgical Instrumentation, Inc., Antioch, TN (US)

(*) Notice: Subject to any disclaimer, the term of this patent is extended or adjusted under 35 U.S.C. 154(b) by 666 days.

(21) Appl. No.: 14/547,749

(22) Filed: Nov. 19, 2014

(65) Prior Publication Data

US 2016/0135817 A1    May 19, 2016

(51) Int. Cl.
*A61B 17/16* (2006.01)
*A61B 90/00* (2016.01)

(52) U.S. Cl.
CPC ... *A61B 17/1611* (2013.01); *A61B 2090/0813* (2016.02)

(58) Field of Classification Search
CPC ............ A61B 17/1608; A61B 17/1611; A61B 17/1604
See application file for complete search history.

(56) References Cited

U.S. PATENT DOCUMENTS

| | | | |
|---|---|---|---|
| 4,777,948 A | 10/1988 | Wright | |
| 4,990,148 A | 2/1991 | Worrick, III et al. | |
| 5,273,519 A | 12/1993 | Koros et al. | |
| 5,323,765 A | 6/1994 | Brown | |
| 5,385,570 A | 1/1995 | Chin et al. | |
| 5,451,227 A | 9/1995 | Michaelson | |
| 5,484,441 A | 1/1996 | Koros et al. | |
| 5,569,258 A * | 10/1996 | Gambale | A61B 17/1611 606/167 |
| 5,653,713 A | 8/1997 | Michelson | |
| 5,766,177 A | 6/1998 | Lucas-Dean et al. | |
| 6,126,674 A * | 10/2000 | Janzen | A61B 17/1611 606/1 |
| 6,142,997 A | 11/2000 | Michelson | |
| 6,200,320 B1 | 3/2001 | Michelson | |
| 6,575,977 B1 | 6/2003 | Michelson | |
| 6,991,633 B2 | 1/2006 | Agbodoe | |
| 7,011,663 B2 | 3/2006 | Michelson | |
| 7,014,638 B2 | 3/2006 | Michelson | |

(Continued)

FOREIGN PATENT DOCUMENTS

| | | |
|---|---|---|
| WO | 2007065530 A2 | 6/2007 |
| WO | 2009010192 A2 | 1/2009 |

*Primary Examiner* — Andrew Yang
(74) *Attorney, Agent, or Firm* — Hayes Soloway PC

(57) ABSTRACT

An adjustable rongeur includes a first handle portion pivotally connected to a second handle portion. A shank is connected to the first handle portion at a proximal end of the shank, wherein the shank has a footplate at a distal end thereof. A crossbar is slidably engaged with the shank, wherein the crossbar is connected to the second handle portion, wherein a cutting opening is formed between a distal end of the crossbar and the footplate of the shank. An opening selection actuator is positioned within at least one of the first and second handle portion, wherein the opening selection actuator engages between the first and second handle portions to control a length of the cutting opening.

20 Claims, 10 Drawing Sheets

(56) References Cited

U.S. PATENT DOCUMENTS

| | | |
|---|---|---|
| 7,922,723 B2 | 4/2011 | Michelson |
| 8,048,106 B2 * | 11/2011 | Widmann .......... A61B 17/1611 |
| | | 606/205 |
| 8,241,290 B2 | 8/2012 | Michelson |
| 8,657,823 B2 * | 2/2014 | Agbodoe ........... A61B 17/1608 |
| | | 606/83 |
| 9,089,345 B2 * | 7/2015 | Funnell .............. A61B 17/1611 |
| 2004/0044346 A1 | 3/2004 | Boury |
| 2004/0102783 A1 | 5/2004 | Sutterlin, III et al. |
| 2004/0122433 A1 | 6/2004 | Loubens et al. |
| 2006/0149271 A1 | 7/2006 | Michelson |
| 2008/0161809 A1 | 7/2008 | Schmitz et al. |
| 2009/0062805 A1 | 3/2009 | Casutt |
| 2009/0264939 A9 | 10/2009 | Martz et al. |
| 2010/0179557 A1 | 7/2010 | Husted |
| 2011/0190773 A1 | 8/2011 | Michelson |
| 2011/0190802 A1 | 8/2011 | Mark et al. |
| 2013/0041379 A1 | 2/2013 | Bodor et al. |
| 2013/0150861 A1 | 6/2013 | Agbodoe |

* cited by examiner

ADJUSTABLE RONGEUR

FIELD OF THE DISCLOSURE

The present disclosure is generally related to rongeur and more particularly is related to adjustable rongeurs.

BACKGROUND OF THE DISCLOSURE

The rongeur is a medical instrument used for a variety of purposes. It is particularly useful for removing small amounts of bone, cartilage or other body material from inside small spaces of the knee or between vertebrae. A rongeur usually includes a long fixed shank with an anvil or footplate at its distal end and a handle at its proximal end. A cross bar slideably engages the shank and reciprocates thereon by means of a pivotable second handle. Cutting edges on the distal end of the crossbar bite against the footplate to cut away a small portion of tissue with each reciprocation of the crossbar.

In the current market place, surgeons have access to different rongeurs with typically a fixed opening length, commonly 9 mm or a 14 mm. While a fixed opening length is adequate for certain procedures, other procedures may uses multiple cut sizes repeatedly throughout the procedure, which results in the surgeon having to switch between various independent instruments frequently. In complex surgical operations, having to switch instruments often may results in delays and heightened complexities in performing the surgical techniques due to the instrument selection interruptions, distractions, or deviations of user comfort with a particular instrument. Using multiple fixed sized instruments also necessitates a greater surgical space and additional sterilization of the instruments. And, relative to the patient's health, using more instruments than are necessary in an operation may increase associated health risks with the operation, such as infections from exposure to contaminated instruments.

Thus, a heretofore unaddressed need exists in the industry to address the aforementioned deficiencies and inadequacies.

SUMMARY OF THE DISCLOSURE

Embodiments of the present disclosure provide an adjustable rongeur and related methods. Briefly described, in architecture, one embodiment of the system, among others, can be implemented as follows. The adjustable rongeur includes a first handle portion pivotally connected to a second handle portion. A shank is connected to the first handle portion at a proximal end of the shank, wherein the shank has a footplate at a distal end thereof. A crossbar is slidably engaged with the shank, wherein the crossbar is connected to the second handle portion, wherein a cutting opening is formed between a distal end of the crossbar and the footplate of the shank. An opening selection actuator is positioned within at least one of the first and second handle portion, wherein the opening selection actuator engages between the first and second handle portions to control a length of the cutting opening.

The present disclosure can also be viewed as providing a rongeur apparatus having an adjustable cutting opening. Briefly described, in architecture, one embodiment of the apparatus, among others, can be implemented as follows. The rongeur apparatus having the adjustable cutting opening includes a crossbar slidably engaged with a shank, wherein a cutting opening is formed between a distal end of the crossbar and a distal end of the shank, wherein a movement of the crossbar is controlled by a first handle portion pivotally connected to a second handle portion. An opening selection actuator is positioned within at least one of the first and second handle portion, wherein the opening selection actuator engages between the first and second handle portions to control a length of the cutting opening.

The present disclosure can also be viewed as providing methods of manufacturing an adjustable rongeur. In this regard, one embodiment of such a method, among others, can be broadly summarized by the following steps: pivotally connecting a first handle portion to a second handle portion; connecting a shank to the first handle portion at a proximal end of the shank, wherein the shank has a footplate at a distal end thereof; slidably engaging a crossbar with the shank, wherein the crossbar is connected to the second handle portion, thereby forming a cutting opening between a distal end of the crossbar and the footplate of the shank; and controlling a length of the cutting opening with an opening selection actuator positioned within at least one of the first and second handle portion, wherein the opening selection actuator is engagable between the first and second handle portions.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
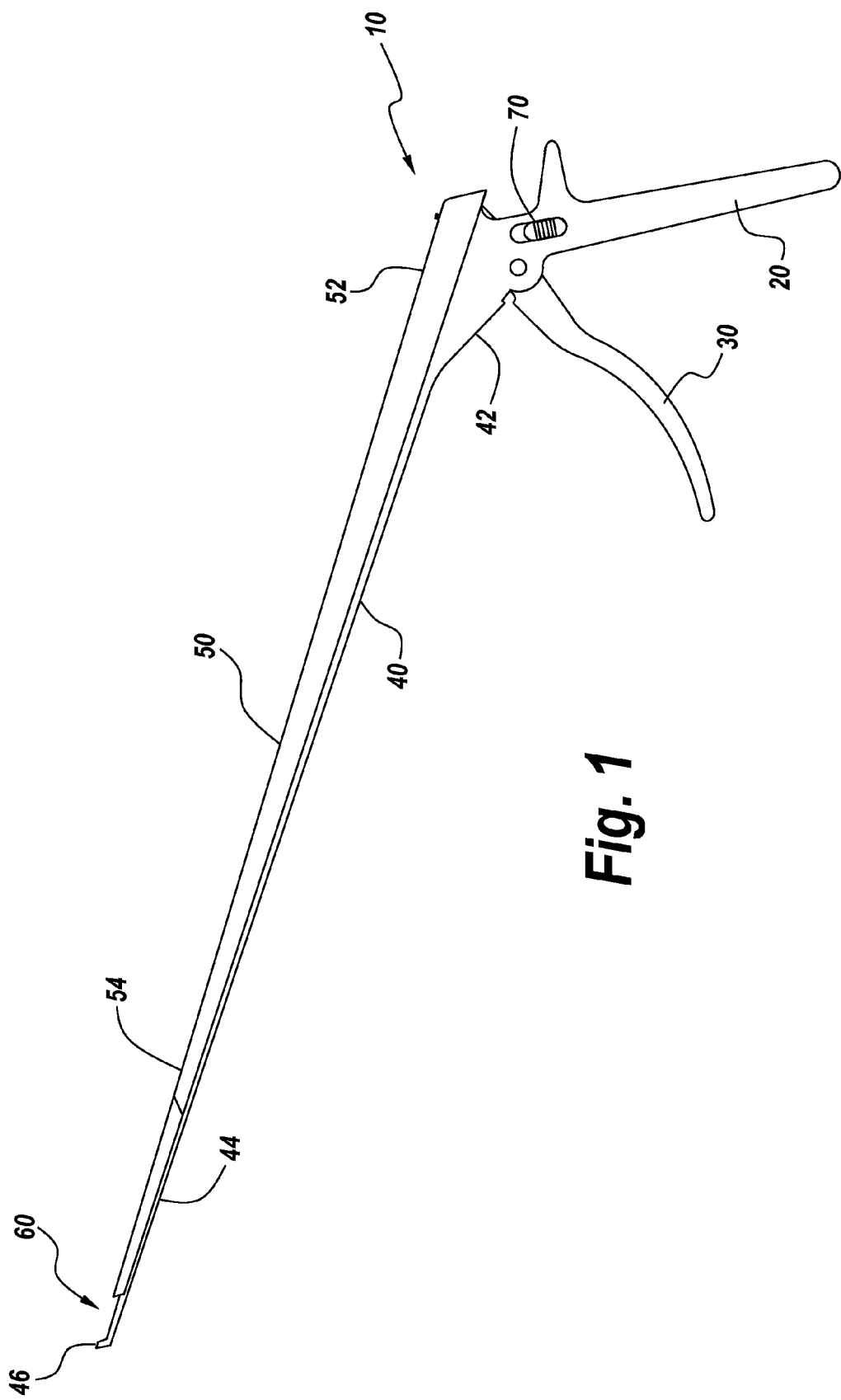
FIG. 1 is an isometric view illustration of an adjustable rongeur, in accordance with a first exemplary embodiment of the present disclosure.

FIG. 1 is an isometric view illustration of an adjustable rongeur 10, in accordance with a first exemplary embodiment of the present disclosure. The adjustable rongeur 10, which may be referred to herein as 'rongeur 10' or 'apparatus 10' includes a first handle portion 20 pivotally connected to a second handle portion 30. A shank 40 is connected to the first handle portion 20 at a proximal end 42 of the shank 40, wherein the shank 40 has a footplate 46 at a distal end 44 thereof. A crossbar 50 is slidably engaged with the shank 40, wherein the crossbar 50 is connected to the second handle portion 30, wherein a cutting opening 60 is formed between a distal end 54 of the crossbar 50 and the footplate 46 of the shank 40. An opening selection actuator 70 is positioned within at least one of the first and second handle portion 20, 30, wherein the opening selection actuator 70 engages between the first and second handle portions 20, 30 to control a length of the cutting opening 60.

Figure 2:
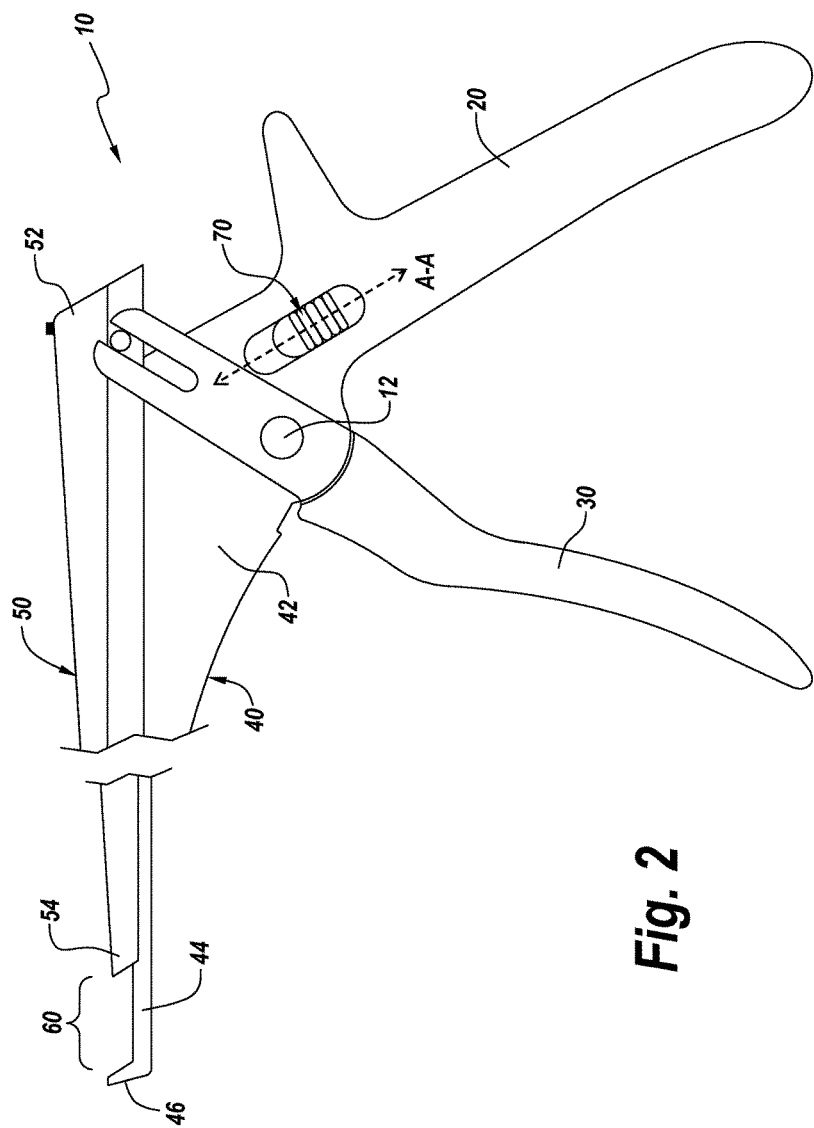
FIG. 2 is a partial cross-sectional view illustration of the rongeur 10 of FIG. 1, in accordance with the first exemplary embodiment of the present disclosure.

FIG. 2 is a partial cross-sectional view illustration of the rongeur 10 of FIG. 1, in accordance with the first exemplary embodiment of the present disclosure. With reference to FIGS. 1-2, the rongeur 10, the first and second handle portions 20, 30 may be connected with a hinged joint 12 or similar joint that allows for pivotal movement between the first and second handle portions 20, 30. The first handle portion 20 is connected to the shank 30 such that the two structures may operate as a substantially unitary structure. For example, the first handle portion 20 may be connected to the shank 30 integrally (shown in FIGS. 1-2) or through a mechanical fastener, or similar structure. The crossbar 40 is movably engaged with the shank 30 using conventional designs, including a mating inverse T-shaped slot formed in the shank 30 with a T-shaped spline extending from the lower surface of the crossbar 40 that engages with the inverse T-shaped slot. As is well known in the industry, the crossbar 40 may move along a direction substantially along the length of the crossbar 40 and shank 30, thereby allowing the cutting opening 60 to open and close.

The opening selection actuator 70 may be positioned in either one or both of the first and second handle portion 20, 30, such that the opening selection actuator 70 engages between the first and second handle portions 20, 30 to control a length of the cutting opening 60. For example, as is shown in FIG. 2, the opening selection actuator 70 may be movable along the exterior surface of the first handle portion 20 substantially along its length. When the second handle portion 30 is pivoted, it may contact the opening selection actuator 70, or a structure extending therefrom, which may physically limit the range of the second handle portion 30. In turn, the limited range of the second handle portion 30 may limit the movement of the crossbar 50, which may directly translate into limited movement of the distal end 54 of the crossbar 50. As the distal end 54 of the crossbar 50 is limited in movement, the cutting opening 60 formed between the distal end 54 of the crossbar 50 and the footplate 46 of the shank 40 may have a length that is relative to the position of the crossbar 50. Thus, the cutting opening 60 may be controlled by the positioning of the opening selection actuator 70.

The opening selection actuator 70 may have a variety of positions, each of which may correlate with a length of the cutting opening 60. For example, as is shown in FIG. 2, the opening selection actuator 70 may be movable between two positions on the first handle portion 20. One position, for example, may correspond with a length of the cutting opening 60 of 9 mm whereas another position may correspond with a length of the cutting opening 60 of 14 mm. Any number of positions correlating to any size of the cutting opening 60 may be utilized with the apparatus 10. The number of positions that the rongeur 10 offers may be dependent on the design of the rongeur 10 and the intended use of the instrument. For example, it is possible to have more complex rongeurs 10 that offer many cutting opening 60 sizes for surgical operations with many cutting operations, or rongeurs 10 with only two cutting opening 60 sizes for operations that require less cutting.

The ability to select between two or more sized cutting openings 60 may provide substantial benefits to medical professionals utilizing the apparatus 10, since it allows them to select the required cutting opening 60 size by mere adjustment of the opening selection actuator 70. In contrast, obtaining different cutting opening 60 sizes using conventional devices required having access to rongeurs with fixed cutting openings and simply using the rongeur that matched the needs. In complex surgical operations, having to switch instruments often results in delays and heightened complexities in performing the surgical techniques due to the instrument selection interruptions.

Figure 3:
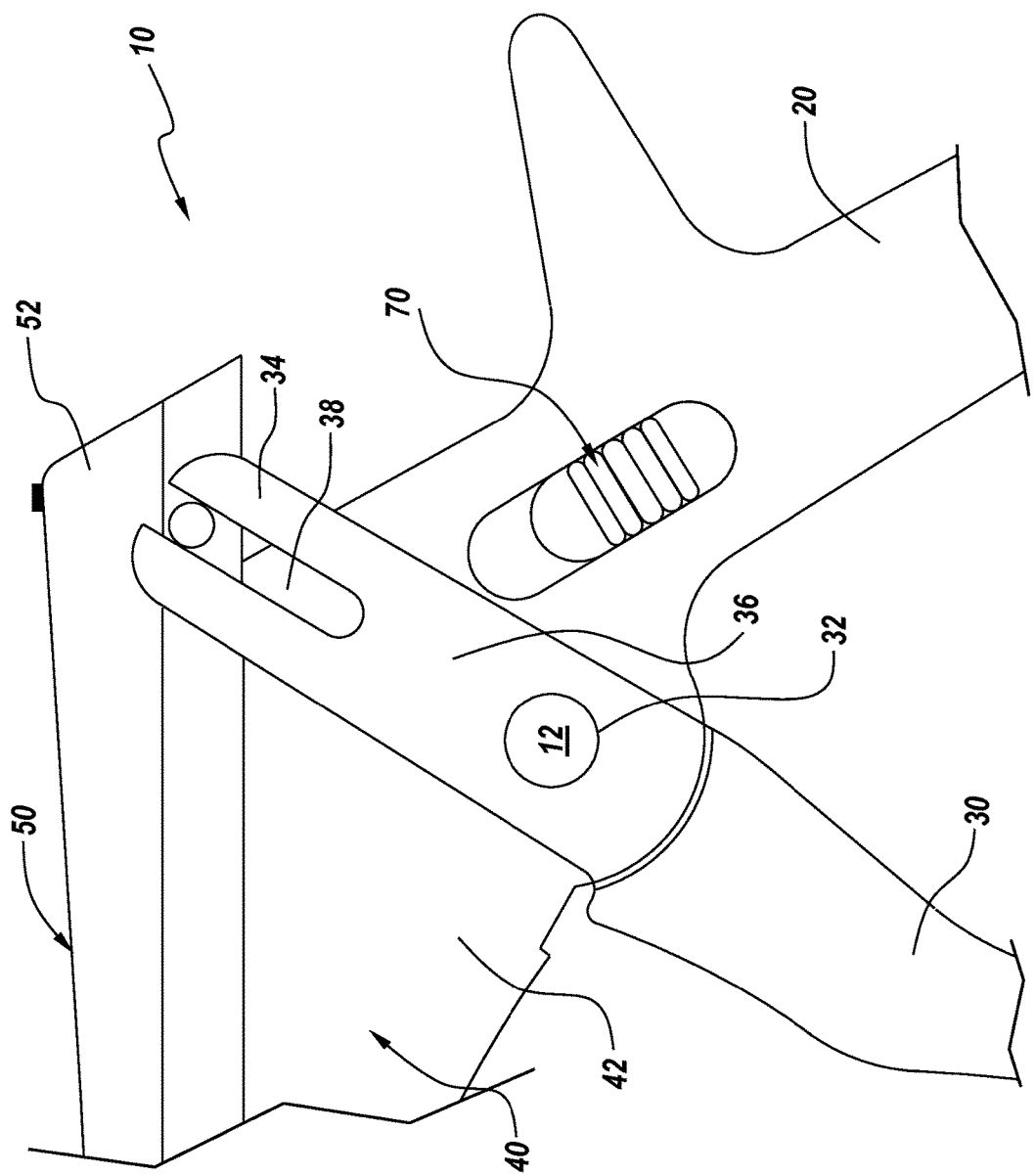
FIG. 3 is an enlarged, partial cross-sectional view illustration of the rongeur of FIG. 2, in accordance with the first exemplary embodiment of the present disclosure.
Figure 4:
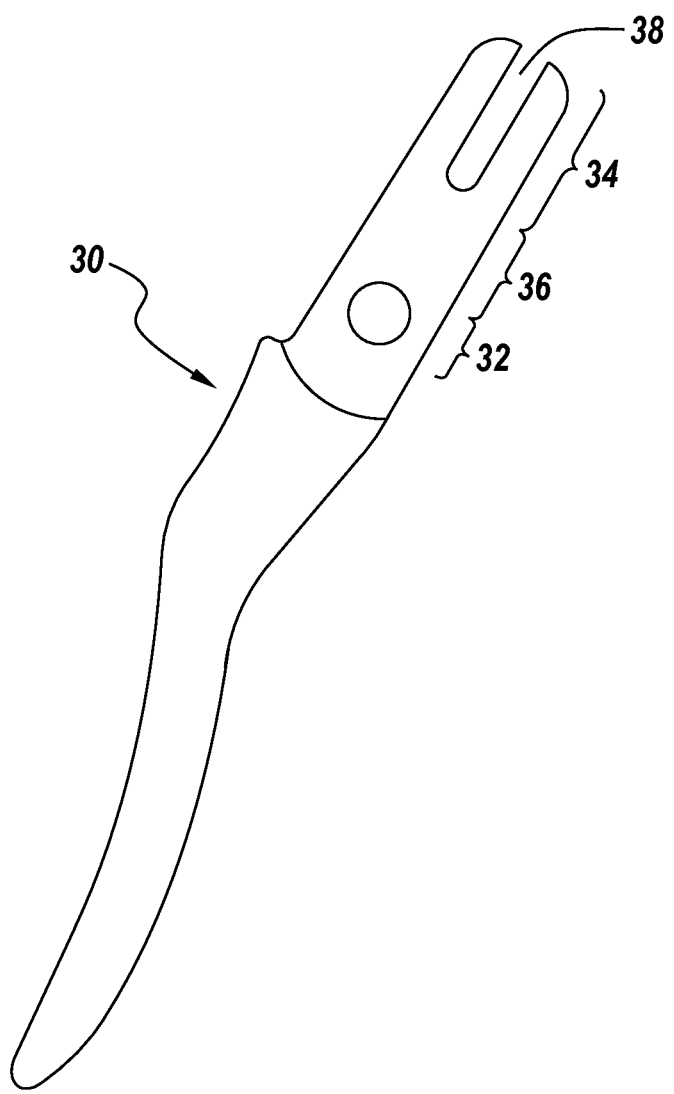
FIG. 4 is a plan view illustration of the second handle portion of the rongeur of FIG. 2, in accordance with the first exemplary embodiment of the present disclosure.

FIG. 3 is an enlarged, partial cross-sectional view illustration of the rongeur 10 of FIG. 2, in accordance with the first exemplary embodiment of the present disclosure. FIG. 4 is a plan view illustration of the second handle portion 30 of the rongeur 10 of FIG. 2, in accordance with the first exemplary embodiment of the present disclosure. Relative to FIGS. 1-4, the second handle portion 30 may comprises a pivot point 32 which substantially corresponds to the hinged joint 12, a crossbar connection portion 34 which engages with the crossbar 60, and a limiting portion 36 which may contact the opening selection actuator 70 to control the length of the cutting opening 60. As is shown in FIGS. 3-4, the limiting portion 36 may be positioned between the pivot point 32 and the crossbar connection portion 34, however in other designs the relative positioning may vary. The crossbar connection 34 of the second handle portion 30 may engage with the crossbar 50 using a slot 38 which receives a pin 56 within the proximal end 52 of the crossbar 50. The pin 56 may move along the length of the slot 38 as the second handle portion 30 is pivoted and as the crossbar 50 moves slideably relative to the shank 40.

As is shown in detail in FIG. 3, the opening selection actuator 70 may contact the limiting portion 36 of the second handle portion 30 to physically retain it from moving beyond a predetermined range. The opening selection actuator 70, for example, can be moved towards the limiting portion 36 such that it is positioned in an upper position on the first handle portion 20 or moved further away from the limiting portion 36 to a lower position (as is shown in FIG.

3). The upper position may correlate into a smaller range of the second handle portion 30, since the limiting portion 36 will contact the opening selection actuator 70 in a shorter distance of movement, as compared to a lower position of the opening selection actuator 70, which allows for a greater range of motion of the second handle portion 30. Accordingly, this upper position of the opening selection actuator 70 may provide for a smaller cutting opening 60 length (FIGS. 1-2) in comparison to the lower position of the opening selection actuator 70.

Figure 5:
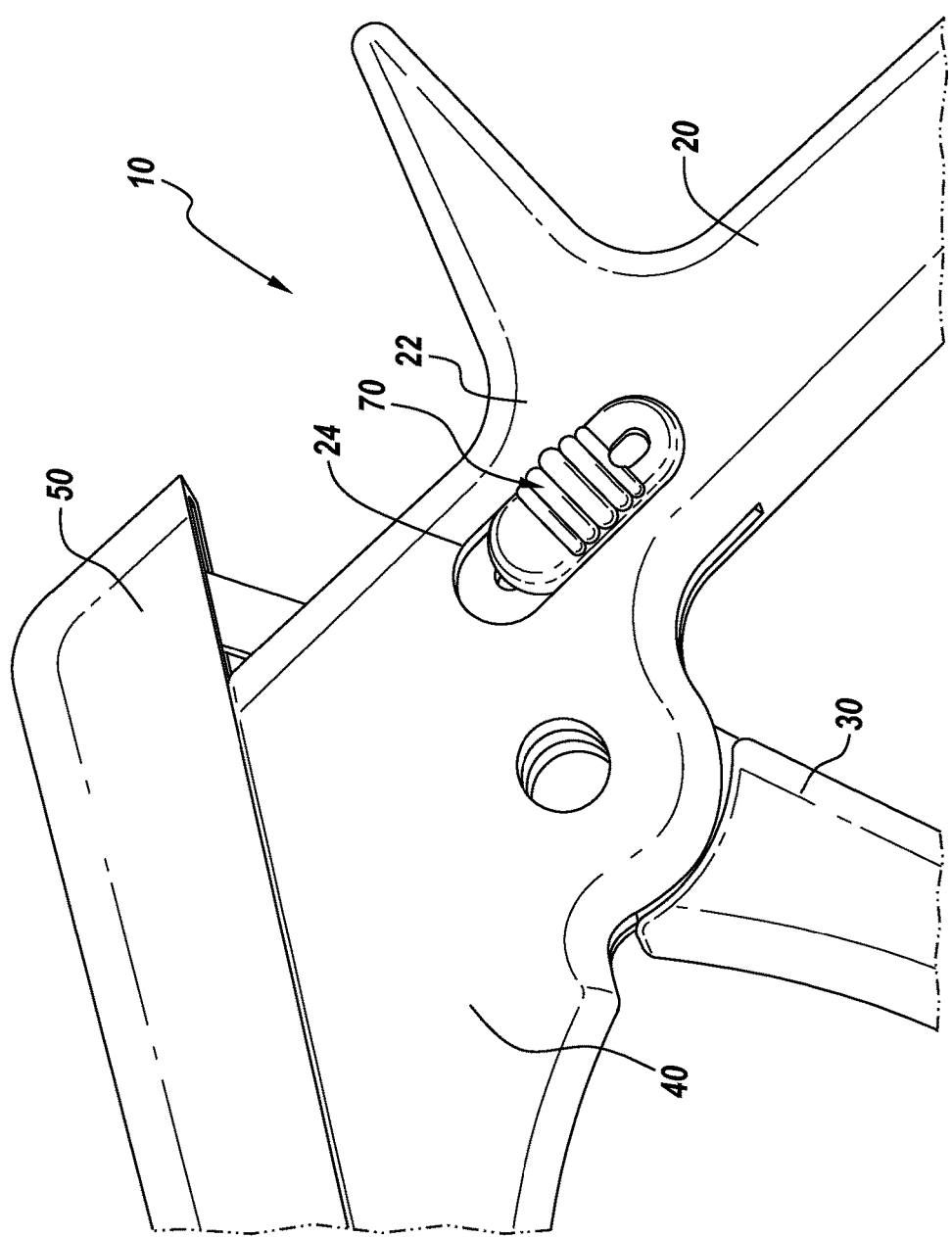
FIG. 5 is an isometric view illustration of the rongeur of FIG. 1, in accordance with the first exemplary embodiment of the present disclosure.

FIG. 5 is an isometric view illustration of the rongeur 10 of FIG. 1, in accordance with the first exemplary embodiment of the present disclosure. As is illustrated in FIG. 5, the opening selection actuator 70 may be positioned on an exterior surface 22 of the first handle portion 20 such that it is readily accessible to a user of the rongeur 10. For example, as the user grasps the first and second handle portions 20, 30 between their palm and their fingers of their right hand, for example, the opening selection actuator 70 may be easily moved between positions with the users thumb. The opening selection actuator 70 may be positioned within a blind slot 24 formed within the first handle portion 20, such that the opening selection actuator 70 fits at least partially within the blind slot 24. The blind slot 24 may be characterized as a hole within the first handle portion 20 that is in the shape of an elongated slot, such as a racetrack shape, which has a closed bottom surface along at least a portion of the hole. The opening selection actuator 70 may be movable within the blind slot 24, which may be sized to substantially define the range of positions of the opening selection actuator 70.

Figure 6:
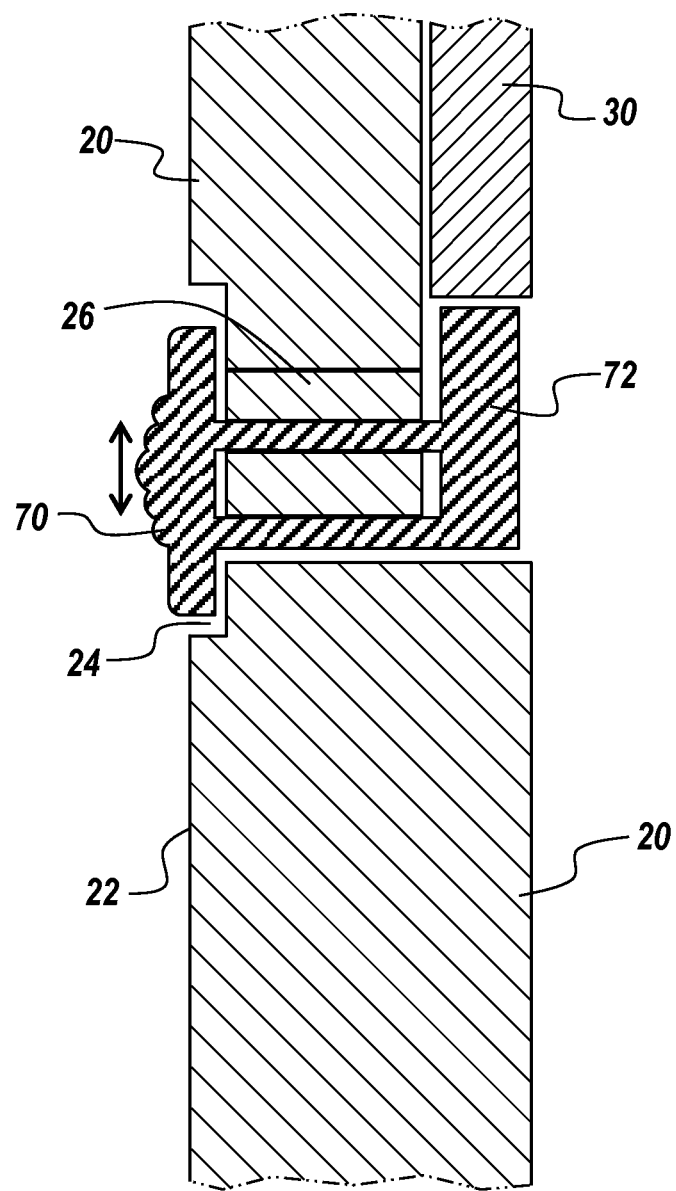
FIG. 6 is a cross-sectional view illustration of the rongeur of FIG. 2 along the line A-A, in accordance with the first exemplary embodiment of the present disclosure.

FIG. 6 is a cross-sectional view illustration of the rongeur 10 of FIG. 2 along the line A-A, in accordance with the first exemplary embodiment of the present disclosure. The opening selection actuator 70 may be positioned on the exterior surface 22 of the first handle portion 20 but may also be positioned at least partially through the first handle portion 20. As is shown in FIG. 6, the opening selection actuator 70 may extend through the first handle portion 20 through a hole 26 within the bottom of the blind slot 24 and may be connected to a limiting plate 72 which is positioned to contact the limiting portion 36 (FIGS. 4-5) of the second handle portion 30. As the opening selection actuator 70 is moved within the blind slot 24, the limiter plate 72 may be moved to adjust the position at which it will contact the second handle portion 30. The opening selection actuator 70 may remain in a position with a low tolerance fit with the first handle portion 20, such that heightened friction prevents movement of the opening selection actuator 70 when the second handle portion 30 contacts the limiter plate 72. Various designs for ensure the appropriate level of friction to prevent unintended movement of the opening selection actuator 70 may be employed.

Figure 7A:
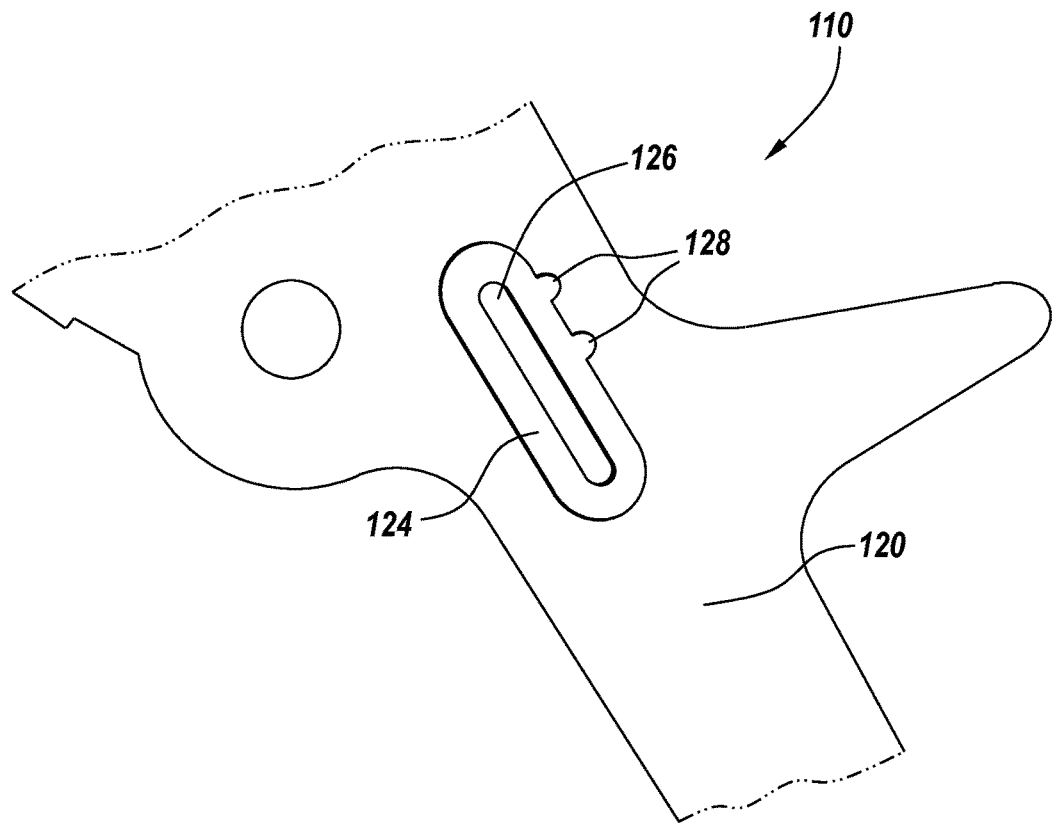
FIG. 7A is a partial plan view illustration of the first handle portion of an adjustable rongeur, in accordance with a second exemplary embodiment of the present disclosure.
Figure 7B:
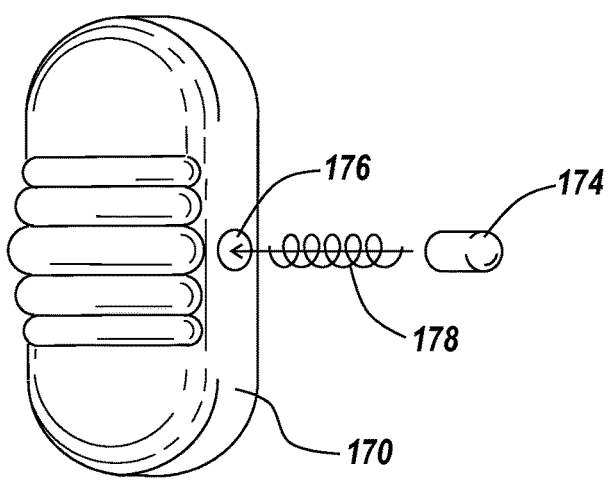
FIG. 7B is an exploded isometric view illustration of the opening selection actuator of the rongeur, in accordance with the second exemplary embodiment of the present disclosure.

FIG. 7A is a partial plan view illustration of the first handle portion 120 of an adjustable rongeur 110, in accordance with a second exemplary embodiment of the present disclosure. FIG. 7B is an exploded isometric view illustration of the opening selection actuator 170 of the rongeur 110, in accordance with the second exemplary embodiment of the present disclosure. It is noted that the adjustable rongeur 110 of the second exemplary embodiment, which may be referred to herein as 'rongeur 110' or 'apparatus 110', may include any of the features, structures, functions, or characteristics disclosed relative to any other embodiment herein, and that all features, structures, functions, or characteristics of other embodiments of this disclosure are considered to be disclosed relative to the second exemplary embodiment.

FIG. 7A illustrates the first handle portion 120 which has the blind slot 124 formed therein. Similar to the disclosure of FIG. 6, the blind slot 124 may include a hole 126 within a portion of the blind slot 124 which allows for the opening selection actuator 170 to be retained to the first handle portion 120 as well as control contact with the second handle portion (not shown). In addition to or in place of retaining the opening selection actuator 170 with friction, the rongeur 110 may include a biasable pin 174 which is positionable within a receiving hole 176 within the side of the opening selection actuator 170, as is shown in FIG. 7B. A spring 178 may be positioned between the biasable pin 174 and the opening selection actuator 170 to bias the biasable pin 174 outwards from the opening selection actuator 170.

When the opening selection actuator 170 with the biasable pin 174 of FIG. 7B is positioned within the blind slot 124 of FIG. 7A, the biasable pin 174 may be biased into positioning slots 128 along the edge of the blind slot 124, thereby positioning the opening selection actuator 170 within a position corresponding to an appropriate positioning slot 128. In use, the spring 178 and the shape of the biasable pin 174 may be sufficiently retained within the positioning slot 128 to prevent inadvertent movement of the opening selection actuator 170. However, when the user desires to change the positioning of the opening selection actuator 170, the user may apply a force to the opening selection actuator 170 which overcomes the resiliency of the spring 178 and allows the biasable pin 174 to retract within the receiving hole 176, thereby allowing the opening selection actuator 170 to move between positions. It is noted that the shape of the biasable pin 174 and the shape of the positioning slots 128 may influence the ease of movement of the opening selection actuator 170.

Figure 8A:
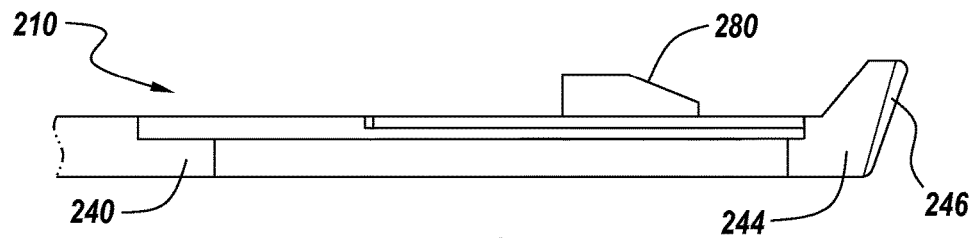
FIG. 8A is a schematic side view illustration of the tapered bone ejector for use with the rongeur, in accordance with a third exemplary embodiment of the present disclosure.
Figure 8B:
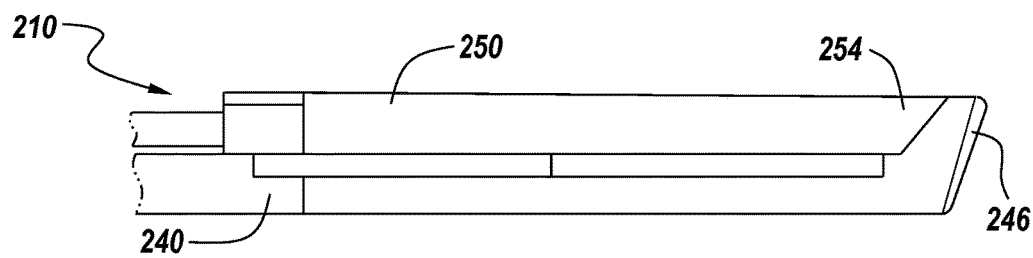
FIGS. 8B-8D are side view illustrations of the tapered bone ejector for use with the rongeur of FIG. 8A in various positions, in accordance with the third exemplary embodiment of the present disclosure.
Figure 8C:
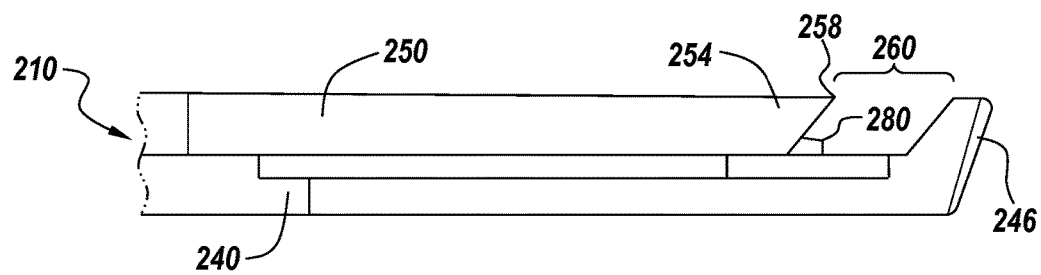
Figure 8D:
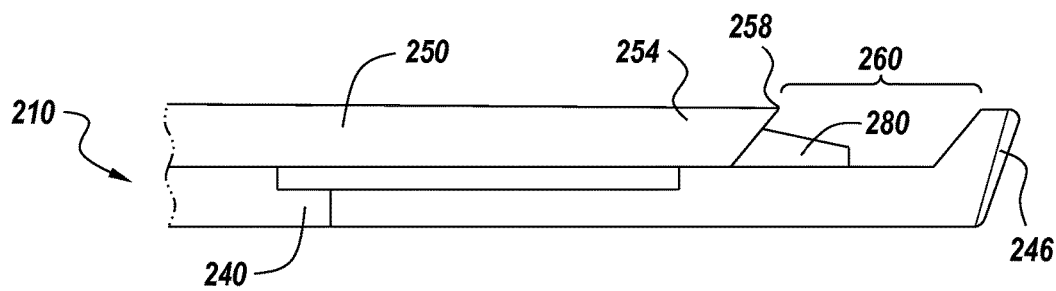

FIG. 8A is a schematic side view illustration of the tapered bone ejector for use with the rongeur 210, in accordance with a third exemplary embodiment of the present disclosure. FIGS. 8B-8D are side view illustrations of the tapered bone ejector for use with the rongeur 210 of FIG. 8A in various positions, in accordance with the third exemplary embodiment of the present disclosure. It is noted that the adjustable rongeur 210 of the third exemplary embodiment, which may be referred to herein as 'rongeur 210' or 'apparatus 210', may include any of the features, structures, functions, or characteristics disclosed relative to any other embodiment herein, and that all features, structures, functions, or characteristics of other embodiments of this disclosure are considered to be disclosed relative to the third exemplary embodiment.

The rongeur 210 may include a tapered bone ejector 280 positioned on the shank 240 at least partially within the cutting opening 260. The tapered bone ejector 280 may allow for bone ejection through the adjustable cutting opening 260 without comprising the clearance of the cutting opening 260 for a shorter length. The tapered bone ejector 280 may include an angled protrusion positioned on an upper surface of the shank 240 proximate to the distal end 244 of the shank 240, as is shown in FIG. 8A. The angled size and shape of the tapered bone ejector 280 may be selected to contact a removed bone portion after it is cut away from the patient in the cutting opening 260 and eject the bone portion from the rongeur 210. This action allows the rongeur 210 to be used continually without experiencing blockages due to bone pieces and without having to retract the crossbar 250 to the fully open position between cuts.

As is shown in FIG. 8B, the tapered bone ejector 280 may be covered by the crossbar 250 when the cutting opening 260 (FIGS. 8C-8D) is concealed by the crossbar 250, e.g., the crossbar 250 may be movable over the tapered bone ejector 280 between covered and non-covered positions. The covered position may correspond to the cutting edge 258 of the crossbar 250 being in contact with the footplate 246 of the shank 240. When the crossbar 250 is retracted after a cut, the user may desire to only withdraw the crossbar 250 a short distance to partially open the cutting opening 260, as opposed to opening the cutting opening 260 to the largest size available. For example, as is shown in FIG. 8C, the crossbar 250 may be opened to provide a 9 mm sized cutting opening 260. When the crossbar 250 is withdrawn, the edge of the tapered bone ejector 280 may contact any bone pieces or particulate on the cutting edge 258 and eject them from the cutting opening 260. Additionally, the tapered bone ejector 280 allows for ejection of bone particulate in the same manner when the crossbar 250 is opened to expose a larger cutting opening 260, such as a 14 mm opening as is shown in FIG. 8D.

Figure 9A:
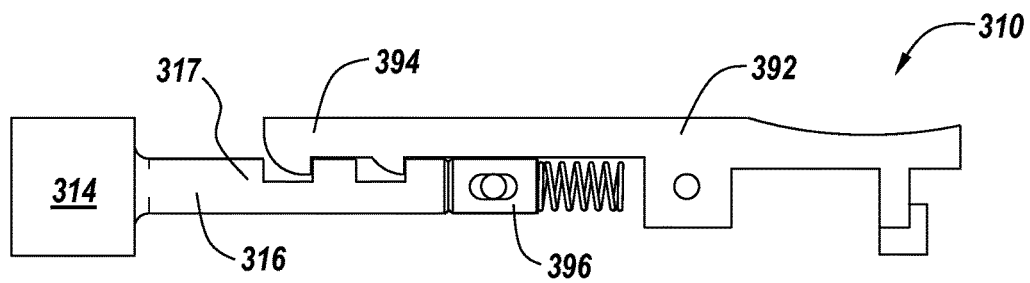
FIGS. 9A-9D are cross-sectional side view illustrations of the latch mechanism for use with a rongeur with removable tips, in accordance with a fourth exemplary embodiment of the present disclosure.
Figure 9B:
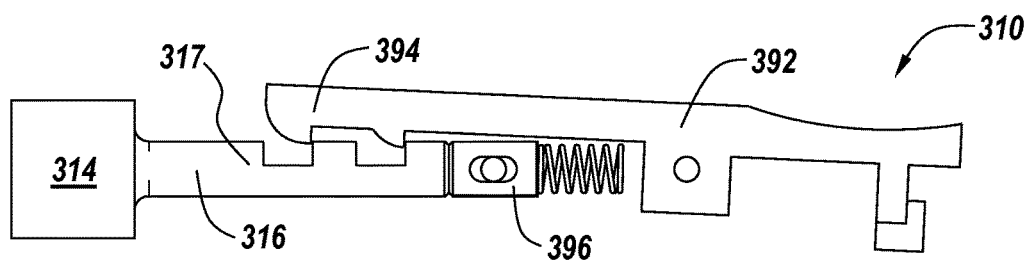
Figure 9C:
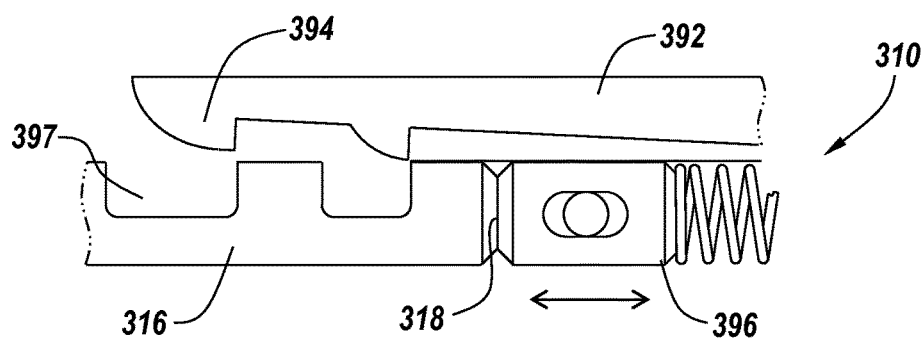
Figure 9D:
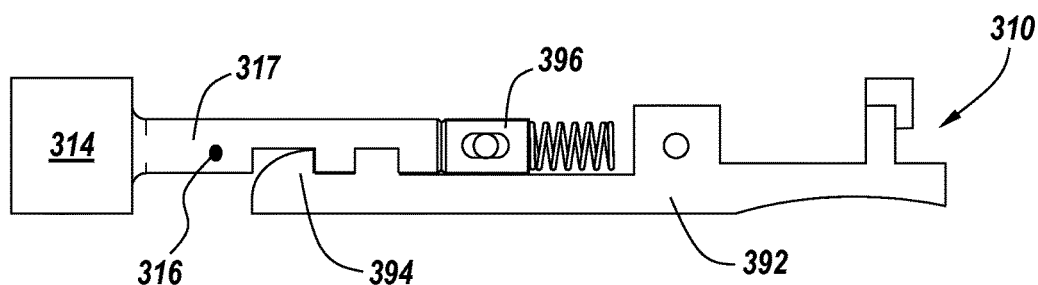

FIGS. 9A-9D are cross-sectional side view illustrations of the latch mechanism 390 for use with a rongeur 310 with removable tips 314, in accordance with a fourth exemplary embodiment of the present disclosure. FIG. 9D is an inverted view of the latch mechanism 390 for use with a rongeur 310 with removable tips 314 shown in FIGS. 9A-9C. It is noted that the adjustable rongeur 310 of the fourth exemplary embodiment, which may be referred to herein as 'rongeur 310' or 'apparatus 310', may include any of the features, structures, functions, or characteristics disclosed relative to any other embodiment herein, and that all features, structures, functions, or characteristics of other embodiments of this disclosure are considered to be disclosed relative to the third exemplary embodiment.

As is shown in FIGS. 9A-9D, the rongeur 310 may include removable tips 314 for either of the shank or crossbar members, such the distal ends of the shank and/or crossbar are formed on the removable tips 314. The removable tip 314 illustrated in FIGS. 9A-9D may include a shaft 316 with a plurality of slots 317 therein. The slots 317 may engage with the latch mechanism 390 which is formed on the crossbar or shank, to secure the removable tip 314 to the crossbar or shank, respectively. The removable tip 314 may be retained to the latch mechanism 390 by a mating between the hooks 394 on a lever 392 of the latch mechanism 390 with the slots 317 of the shaft 316.

The latch mechanism 390 may operate based on a pivoting of the lever 392 on a pivot point 396, thereby allowing the hooks 394 to engage with the slots 317 of the shaft 316 when the shaft 316 is inserted into either the crossbar or shank that the latch mechanism 390 is located in. As is shown in FIG. 9A, the lever 392 may be positioned clear from the shaft 316 whereas in FIG. 9B, the lever 392 is moved closer to a mated position with the slots 317 on the shaft 316. In FIG. 9C, the lever 392 is shown in the mated position with the slots 317 on the shaft 316, such that the hooks 394 retain the shaft 316 in place against a spring-biased pusher 396. It is noted that FIG. 9C illustrates the mated position, but not the fully mated position, as the fully mated position between the hooks 394 and the slots 317 will result in full engagement of the hooks 394 into the slots 317. A spring on a proximal end of the lever 392 may act to bias the hooks 394 towards the location of the shaft 316, and subsequently retain the lever 392 in the closed position, shown in FIG. 9D.

The latch mechanism 390 may be engagable between at least one of a shank tip and a shank body, and a crossbar tip and a crossbar body, depending on whether the rongeur 310 utilizes removable tips 314 for one or both of the shank and crossbar. To aid in engagement between the removable tips 314 and the rongeur 310, the latch mechanism 390 may use the spring-biased pusher 396 which contacts a mating face 318 (FIG. 9C) of the removable tip 314, i.e., of the shank tip or the crossbar tip. The spring-biased pusher 396 may ensure that the mating face 318 of the removable tip 314 and the latch mechanism 390 remain in contact. The spring-biased pusher may also allow clearance when required during a connection or disconnection of the removable tip 314 from the rongeur 310.

Figure 10:
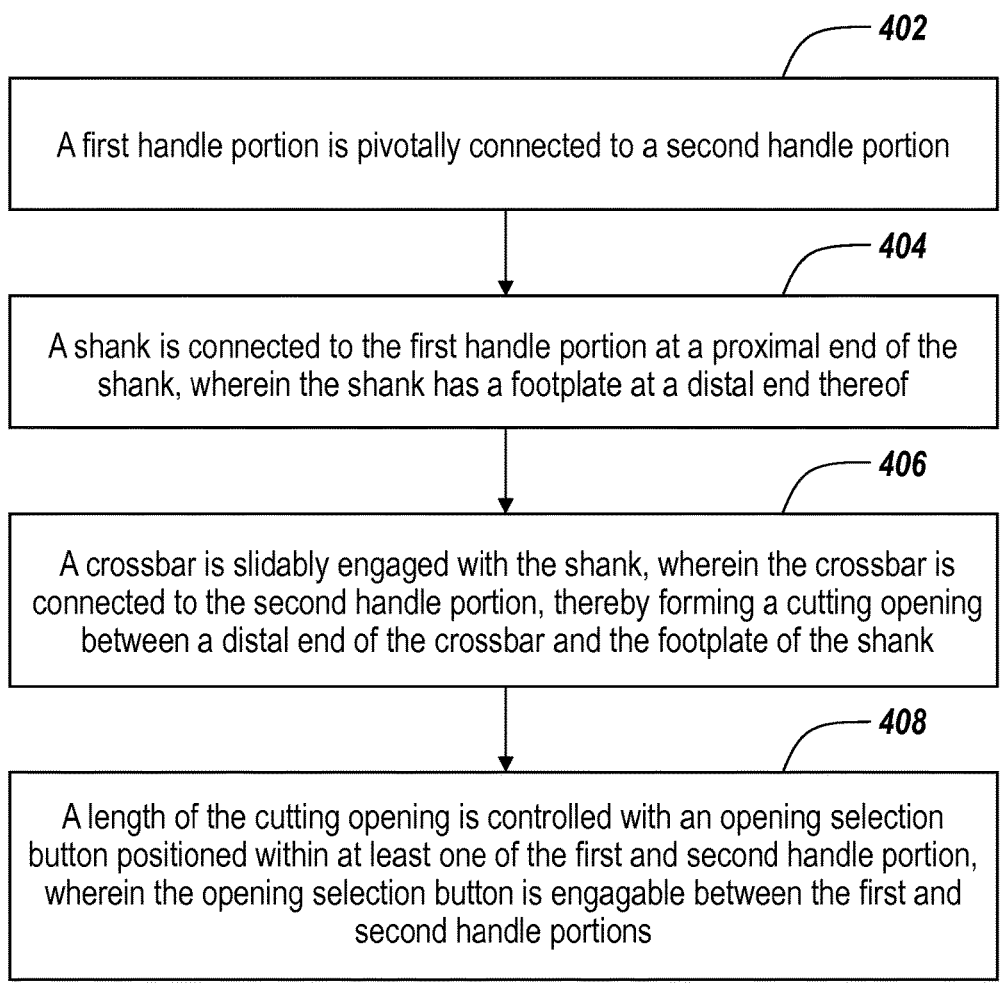
FIG. 10 is a flowchart illustrating a method of manufacturing an adjustable rongeur 10 in accordance with the first exemplary embodiment of the disclosure.

FIG. 10 is a flowchart 400 illustrating a method of manufacturing an adjustable rongeur 10 in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 402, a first handle portion is pivotally connected to a second handle portion. A shank is connected to the first handle portion at a proximal end of the shank, wherein the shank has a footplate at a distal end thereof (block 404). A crossbar is slidably engaged with the shank, wherein the crossbar is connected to the second handle portion, thereby forming a cutting opening between a distal end of the crossbar and the footplate of the shank (block 406). A length of the cutting opening is controlled with an opening selection actuator positioned within at least one of the first and second handle portion, wherein the opening selection actuator is engagable between the first and second handle portions (block 408).

It is noted that the method may include any additional steps, processes, functions, or structures, including any steps, processes, functions, or structures disclosed relative to FIGS. 1-9D herein. For example, the method may include forming a blind slot within the first handle, wherein the opening selection actuator fits at least partially within the blind slot. The second handle portion may further comprises a pivot point, a crossbar connection portion, and a limiting portion, wherein the crossbar connection portion engages with a proximal end of the crossbar. The crossbar connection of the second handle portion may further comprises a slot, wherein a pin within the proximal end of the crossbar engages with the slot.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:
1. An adjustable rongeur comprising:
   a first handle portion pivotally connected to a second handle portion;
   a shank connected to the first handle portion at a proximal end of the shank, wherein the shank has a footplate at a distal end thereof;
a crossbar slidably engaged with the shank, wherein the crossbar is connected to
the second handle portion, wherein a cutting opening is formed between a distal end of
the crossbar and the footplate of the shank; and
an opening selection actuator positioned within at least one of the first and second
handle portion, wherein the opening selection actuator engages between the first and
second handle portions to control a length of the cutting opening while continuing to
slidably engage the crossbar with the shank.

2. The apparatus of claim 1, wherein the shank is integrally connected to the first handle portion.

3. The apparatus of claim 1, wherein the opening selection actuator is positioned on an exterior surface of the first handle portion and is positioned through the first handle portion.

4. The apparatus of claim 3, wherein the opening selection actuator is frictionally retained on the exterior surface of the first handle.

5. The apparatus of claim 1, further comprising a blind slot formed within the first handle, wherein the opening selection actuator fits at least partially within the blind slot.

6. The apparatus of claim 1, wherein the opening selection actuator is movable between at least two positions, wherein the at least two positions correspond to at least two different lengths of the cutting opening.

7. The apparatus of claim 1, wherein the second handle portion further comprises a pivot point, a crossbar connection portion, and a limiting portion.

8. The apparatus of claim 7, wherein the opening selection actuator contacts the limiting portion of the second handle portion to control the length of the cutting opening.

9. The apparatus of claim 7, wherein the crossbar connection of the second handle portion further comprises a slot, wherein a pin within the proximal end of the crossbar engages with the slot.

10. The apparatus of claim 1, wherein the shank further comprises a shank tip removable from a shank body, wherein the shank tip includes the footplate.

11. The apparatus of claim 1, wherein the crossbar further comprises a crossbar tip removable from a crossbar body, wherein the crossbar tip includes a cutting edge.

12. The apparatus of claim 1, wherein the shank further comprises a shank tip removable from a shank body, wherein the shank tip includes the footplate, and wherein the crossbar further comprises a crossbar tip removable from a crossbar body, wherein the crossbar tip includes a cutting edge, further comprising a latch mechanism engagable between at least one of: the shank tip and the shank body; and the crossbar tip and the crossbar body, the latch mechanism having a spring-biased pusher, wherein the spring-biased pusher contacts a mating face of at least one of the shank tip and the crossbar tip, respectively.

13. The apparatus of claim 12, wherein the latch mechanism further comprises a spring-biased pivoting latch having at least one hook on a distal end thereof, wherein the at least one hook is engagable with at least one slot formed within at least one of the shank tip and the crossbar tip, respectively.

14. The apparatus of claim 1, further comprising a tapered bone ejector positioned on the shank at least partially within the cutting opening.

15. The apparatus of claim 14, wherein the crossbar is movable over the tapered bone ejector between covered and non-covered positions.

16. An rongeur apparatus having an adjustable cutting opening, the rongeur apparatus comprising:
a crossbar slidably engaged with a shank, wherein a cutting opening is formed between a distal end of the crossbar and a distal end of the shank, wherein a movement of the crossbar is controlled by a first handle portion pivotally connected to a second handle portion; and
an opening selection actuator positioned within at least one of the first and
second handle portion, wherein the opening selection actuator engages between the first and second handle portions to control a length of the cutting opening while continuing to slidably engage the crossbar with the shank.

17. A method of manufacturing an adjustable rongeur, the method comprising the steps of:
pivotally connecting a first handle portion to a second handle portion; connecting a shank to the first handle portion at a proximal end of the shank,
wherein the shank has a footplate at a distal end thereof;
slidably engaging a crossbar with the shank, wherein the crossbar is connected to the second handle portion, thereby forming a cutting opening between a distal end of the crossbar and the footplate of the shank; and
controlling a length of the cutting opening while continuing to slidably engage the crossbar with the shank with an opening selection actuator positioned within at least one of the first and second handle portion, wherein the opening selection actuator is engagable between the first and second handle portions.

18. The method of claim 17, further comprising the step of forming a blind slot within the first handle portion, wherein the opening selection actuator fits at least partially within the blind slot.

19. The method of claim 17, wherein the second handle portion further comprises a pivot point, a crossbar connection portion, and a limiting portion, wherein the crossbar connection portion engages with a proximal end of the crossbar.

20. The method of claim 19, wherein the crossbar connection of the second handle portion further comprises a slot, wherein a pin within the proximal end of the crossbar engages with the slot.

* * * * *